United States Patent
Biggs

[11] Patent Number: 6,146,355
[45] Date of Patent: *Nov. 14, 2000

[54] STEERABLE CATHETER

[75] Inventor: Robert C. Biggs, Alpharetta, Ga.

[73] Assignee: Myelotec, Inc., Rosewell, Ga.

[ * ] Notice: This patent is subject to a terminal disclaimer.

[21] Appl. No.: 09/126,863

[22] Filed: Jul. 31, 1998

Related U.S. Application Data

[63] Continuation-in-part of application No. 08/777,548, Dec. 30, 1996, Pat. No. 6,030,360.

[51] Int. Cl.$^7$ .................................................. A61M 37/00
[52] U.S. Cl. ..................................... 604/95.01; 604/95.04
[58] Field of Search ................................. 604/95, 49, 53, 604/54, 264, 523, 524, 525, 528

[56] References Cited

U.S. PATENT DOCUMENTS

| | | | |
|---|---|---|---|
| D. 343,678 | 1/1994 | Snoke et al. | D24/112 |
| D. 349,340 | 8/1994 | Snoke et al. | D24/138 |
| 3,397,840 | 8/1968 | Sullivan et al. | 525/221 |

(List continued on next page.)

FOREIGN PATENT DOCUMENTS

| | | |
|---|---|---|
| 0343094 | 11/1989 | European Pat. Off. . |
| 0370158 | 5/1990 | European Pat. Off. . |
| 0815895A1 | 1/1998 | European Pat. Off. ....... A61M 25/01 |
| WO88/00810 | 2/1988 | WIPO . |
| WO91/11213 | 8/1991 | WIPO . |
| WO94/01162 | 1/1994 | WIPO . |
| WO96/08993 | 3/1996 | WIPO . |
| WO 96/40309 | 12/1996 | WIPO . |

OTHER PUBLICATIONS

A Method For Epiduroscopy and Spinaloscopy, R. Blomberg, Acta Anaesthesiol Scand 1985, pp. 113–116.
Myeloscopy, International Orthopaedics, Yoshio Ooi et al., Springer–Verlag 1977, pp. 107–111.

(List continued on next page.)

*Primary Examiner*—Wynn Wood Coggins
*Assistant Examiner*—Jennifer Maynard
*Attorney, Agent, or Firm*—Gardner & Groff, P.C.

[57] ABSTRACT

A steerable catheter (310) having a handle, a manifold strain relief (314) securely mounted at a front distal end of the handle, a steering dial (316) rotatably mounted within the handle, the steering dial (316) comprises a steering dial left fastener (316L) and a steering dial right fastener (316R). A lumen extrusion shaft (318) is securely fastened at a rear distal end to the manifold strain relief (314). The lumen extrusion shaft (318) has at least one lumen extrusion shaft large lumen opening (318B) and at least one lumen extrusion shaft small lumen opening (318C) contained therein. A lumen extrusion tip (320) is securely fastened at a front distal end of the lumen extrusion shaft (318) by a lumen extrusion shaft connection (318A). A manifold (334) is securely fastened at a rear end of the manifold strain relief (314). At least one luer lock (324) is securely mounted at a rear distal end of the handle. A steering wire (328) securely fastened at a rear distal end to the steering dial (316). The steering wire (328) is slidably mounted within the manifold (334) and the manifold strain relief (314) and the lumen extrusion shaft (318). The steering wire (328) has a left steering wire (328L) securely fastened at a rear distal end to the steering dial left fastener (316L) and a right steering wire (328R) securely fastened at a rear distal end to the steering dial right fastener (316R). The steering wire (328) is slidably positioned within the at least one lumen extrusion shaft small lumen opening (318C). The steering wire (328) is securely affixed at a front end to the lumen extrusion shaft (318) by a lumen extrusion shaft small lumen attachment (318CA). The steering wire (328) terminates at a front distal end wire flat lumen extrusion tip which is securely mounted within the lumen extrusion tip (320). A catheter body lumen tubing (330) securely fastened at a rear distal end to the least one luer lock (324) and is securely fastened at a front distal end to the at least one lumen extrusion shaft large lumen opening (318B). A front end of the catheter body lumen tubing (330) is securely mounted within the manifold (334).

5 Claims, 8 Drawing Sheets

U.S. PATENT DOCUMENTS

| | | | |
|---|---|---|---|
| 3,470,876 | 10/1969 | Barchilon . | |
| 3,525,561 | 8/1970 | Takahasi . | |
| 3,595,220 | 7/1971 | Kawahara . | |
| 3,605,725 | 9/1971 | Bentov . | |
| 3,892,228 | 7/1975 | Mitsui | 128/4 |
| 4,214,593 | 7/1980 | Imbruce et al. | 128/748 |
| 4,349,014 | 9/1982 | Takamatsu | 128/6 |
| 4,483,326 | 11/1984 | Yamaka et al. | 128/4 |
| 4,508,103 | 4/1985 | Calisi | 128/673 |
| 4,545,374 | 10/1985 | Jacobson | 128/303 R |
| 4,558,691 | 12/1985 | Okada | 128/6 |
| 4,573,448 | 3/1986 | Kambin | 128/1 R |
| 4,601,284 | 7/1986 | Arakawa et al. | 128/6 |
| 4,720,178 | 1/1988 | Nishioka et al. | 350/401 |
| 4,737,142 | 4/1988 | Heckele | 604/95 |
| 4,752,292 | 6/1988 | Lopez et al. | 604/244 |
| 4,776,844 | 10/1988 | Ueda | 604/95 |
| 4,796,615 | 1/1989 | Bullock et al. | 128/202.27 |
| 4,799,474 | 1/1989 | Ueda | 128/4 |
| 4,808,157 | 2/1989 | Coombs | 604/44 |
| 4,902,129 | 2/1990 | Siegmund et al. | 356/241 |
| 4,904,237 | 2/1990 | Janese | 604/28 |
| 4,905,666 | 3/1990 | Fukuda | 128/4 |
| 4,919,653 | 4/1990 | Martinez et al. | 604/117 |
| 4,930,521 | 6/1990 | Metzger et al. | 128/786 |
| 4,934,340 | 6/1990 | Ebling et al. | 128/6 |
| 4,965,319 | 10/1990 | Kawamoto | 525/194 |
| 4,968,298 | 11/1990 | Michelson | 604/36 |
| 4,973,312 | 11/1990 | Andrew | 604/158 |
| 4,983,165 | 1/1991 | Loiterman | 604/95 |
| 4,985,022 | 1/1991 | Fearnot et al. | 604/282 |
| 4,986,262 | 1/1991 | Saito | 128/6 |
| 4,996,974 | 3/1991 | Ciarlei | 128/4 |
| 5,053,046 | 10/1991 | Janese | 606/215 |
| 5,084,043 | 1/1992 | Hertzman et al. | 606/3 |
| 5,085,631 | 2/1992 | Leighton | 604/28 |
| 5,108,364 | 4/1992 | Takezawa et al. | 604/43 |
| 5,131,382 | 7/1992 | Meyer | 128/6 |
| 5,143,475 | 9/1992 | Chikama | 403/291 |
| 5,167,221 | 12/1992 | Chikama | 128/4 |
| 5,168,864 | 12/1992 | Shockey | 128/4 |
| 5,188,594 | 2/1993 | Zilberstein | 604/51 |
| 5,195,541 | 3/1993 | Obenchain | 128/898 |
| 5,198,301 | 3/1993 | Hager et al. | 428/355 |
| 5,199,950 | 4/1993 | Schmitt et al. | 604/95 |
| 5,215,105 | 6/1993 | Kizelshteyn et al. | 128/898 |
| 5,218,970 | 6/1993 | Turnbull et al. | 128/748 |
| 5,226,879 | 7/1993 | Ensminger et al. | 604/93 |
| 5,232,442 | 8/1993 | Johnson et al. | 604/51 |
| 5,244,467 | 7/1993 | Oku | 128/4 |
| 5,256,158 | 10/1993 | Tolkoff et al. | 604/280 |
| 5,284,489 | 2/1994 | Liu et al. | 606/228 |
| 5,289,831 | 3/1994 | Bosley | 128/899 |
| 5,298,571 | 3/1994 | Statz et al. | 525/330.2 |
| 5,308,324 | 5/1994 | Hammerslag et al. | 604/95 |
| 5,342,299 | 8/1994 | Snoke et al. | 604/95 |
| 5,354,266 | 10/1994 | Snoke | 604/28 |
| 5,372,587 | 12/1994 | Hammerslag | 604/95 |
| 5,396,880 | 3/1995 | Kagan et al. | 128/6 |
| 5,399,164 | 3/1995 | Snoke et al. | 604/95 |
| 5,399,165 | 3/1995 | Snoke et al. | 604/95 |
| 5,419,312 | 5/1995 | Arenberg et al. | 128/6 |
| 5,423,311 | 6/1995 | Snoke et al. | 128/6 |
| 5,431,168 | 7/1995 | Webster, Jr. | 128/658 |
| 5,437,636 | 8/1995 | Snoke et al. | 604/95 |
| 5,454,794 | 10/1995 | Narciso et al. | 604/280 |
| 5,456,664 | 10/1995 | Heinzelmann et al. | 604/95 |
| 5,492,530 | 2/1996 | Fischell et al. | 604/49 |
| 5,496,269 | 3/1996 | Snoke | 604/28 |
| 5,507,725 | 4/1996 | Savage et al. | 604/95 |
| 5,507,732 | 4/1996 | McClure et al. | 604/280 |
| 5,516,847 | 5/1996 | Sullivan et al. | 525/221 |
| 5,526,820 | 6/1996 | Khoury | 128/748 |
| 5,531,687 | 7/1996 | Snoke et al. | 604/95 |
| 5,542,924 | 8/1996 | Snoke et al. | 604/95 |
| 5,545,149 | 8/1996 | Brin et al. | 604/265 |
| 5,549,580 | 8/1996 | Diaz | 604/280 |
| 5,556,381 | 9/1996 | Ensminger et al. | 604/93 |
| 5,569,221 | 10/1996 | Houser et al. | 604/282 |
| 5,638,819 | 6/1997 | Manwaring et al. | 128/653.1 |
| 5,658,263 | 8/1997 | Dang et al. | 604/280 |
| 5,662,622 | 9/1997 | Gore et al. | 604/282 |
| 5,779,688 | 7/1998 | Imran et al. | 604/283 |
| 5,857,999 | 1/1999 | Snoke | 604/28 |
| B1 4,919,112 | 12/1993 | Siegmund | 128/4 |

OTHER PUBLICATIONS

Eighteen–Guage Microscopic–Telescopic Needle Endoscope with Electrode Channel, Charles P. Olinger, M.D. and R.L. Ohlhaber, Surgical Neurology, vol. 2, 1974, pp. 151–160.

Myeloscopy: Intraspinal Endoscopy, J. Lawrence Pool, M.D., Surgery, Feb. 1942.

The Spinascope; A New Instrument for Visualizing the Spinal Canal and Its Content, Ellas Lincoln Stern. Medical Record, pp. 31–32 (date unknown).

Percutaneous Evaluation of The Epidural and Subarachnoid Space with a Flexible Fiberscope, James E. Heavner, DVM, PhD, Regional Anesthesia 1991, p. 85.

Bjorn Holmstrom, Epiduroscopic Study of Risk of Catheter Migration Following Dural Puncture by Spiral and Epidural Needles—A Video Presentation, Regional Anesthesia, 1991.

Epidural Balloon Catheter System for Lysing Epidural Adhesions, Grigory Kizelshteyn, M.D., Regional Anesthesia 1991, p. 87.

The Lumber Epidural Space in Patients Examined with Epiduroscopy, Rune G. Blomberg, MD and Sven S. Olsson, MD, Anesth. Analg. 1989, pp. 157–160.

The Dorsomedian Connective Tissue Band in the Lumbar Epidural Space of Humans: An Anatomical Study Using Epiduroscopy in Autopsy Cases, Rune Blomberg, MD, Anesth. Analg, 1986, pp. 747–52.

A Method for Epiduroscopy and Spinaloscopy: Presentation of Preliminary Results, R. Blomberg, Acta Anaesthesiol Scand 1985: 29: 113 to 116.

The Lumbar Epidural Space in Patients Examined with Epiduroscopy, R. Blomberg, Anesthesia and Analgesia, vol. 68, 1989, Supplement, pp. 157–160.

Direct Observation of the Epidural Space with a Flexible Catheter–Secured Epiduroscopic Unit, G. Schutze and H. Kurtze, Journal of the American and European Societies of Regional Anesthesia (1994), pp. 85 to 89.

Catheter Replacement of the Needle in Percutaneous Arteriography, A new technique by Sven Ivar Seldinger. Roentgen Diagnostic Dept. (ca. 1952).

Pain Management in the 21$^{st}$ Century: An Anesthesiologists's Look Into the Crystal Ball, Steven D. Waldman, MD Anesthesiology (1991).

Observation of Spinal Canal and Cisternae with the Newly Developed Small–Diameter, Flexible Fiberscopes Anesthesiology (date unknown).

ASRA News, Aug. 1995, pp. 1–3.

MedPro Month, Dec. 1991, pp. 178–188.

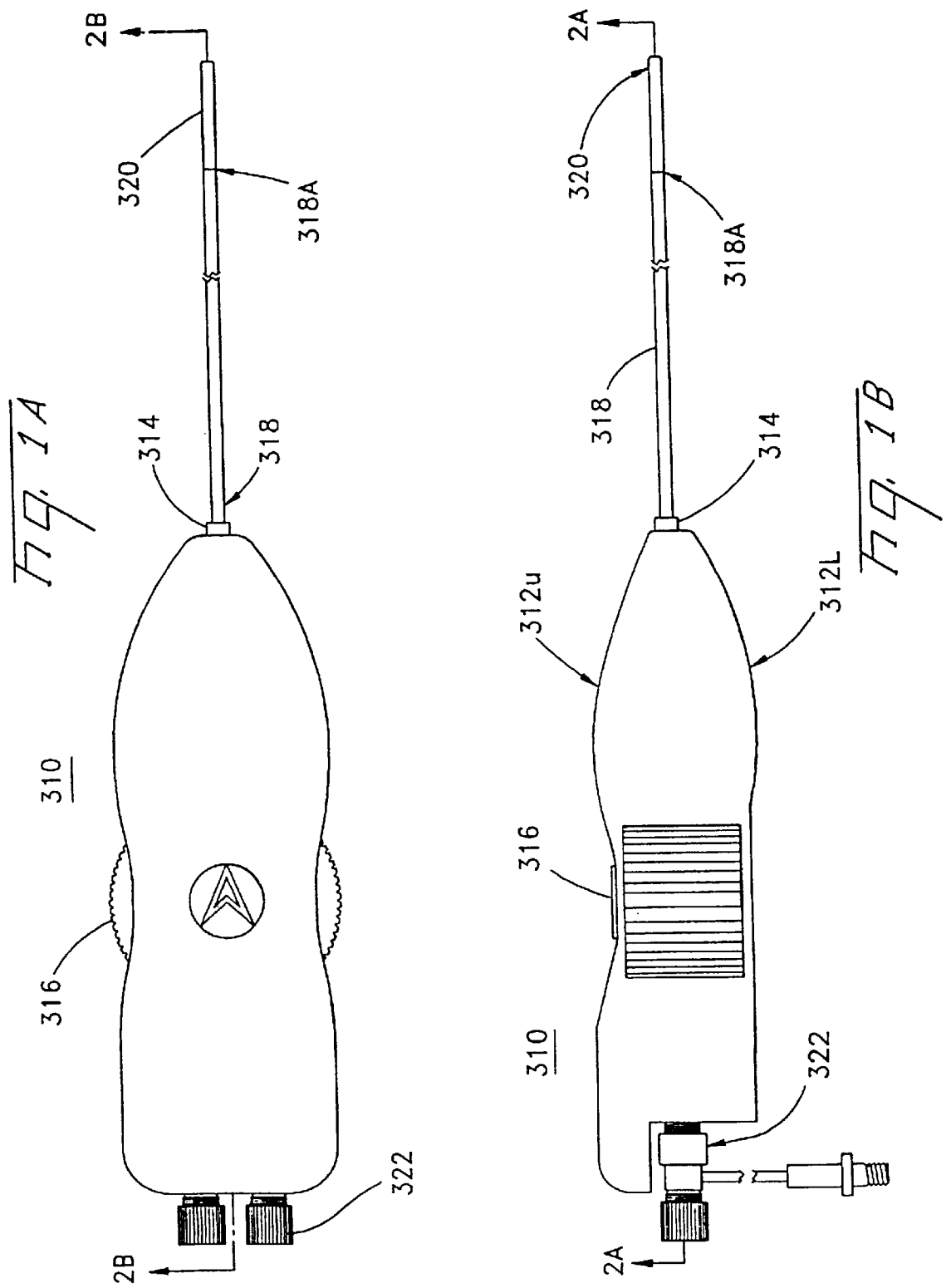

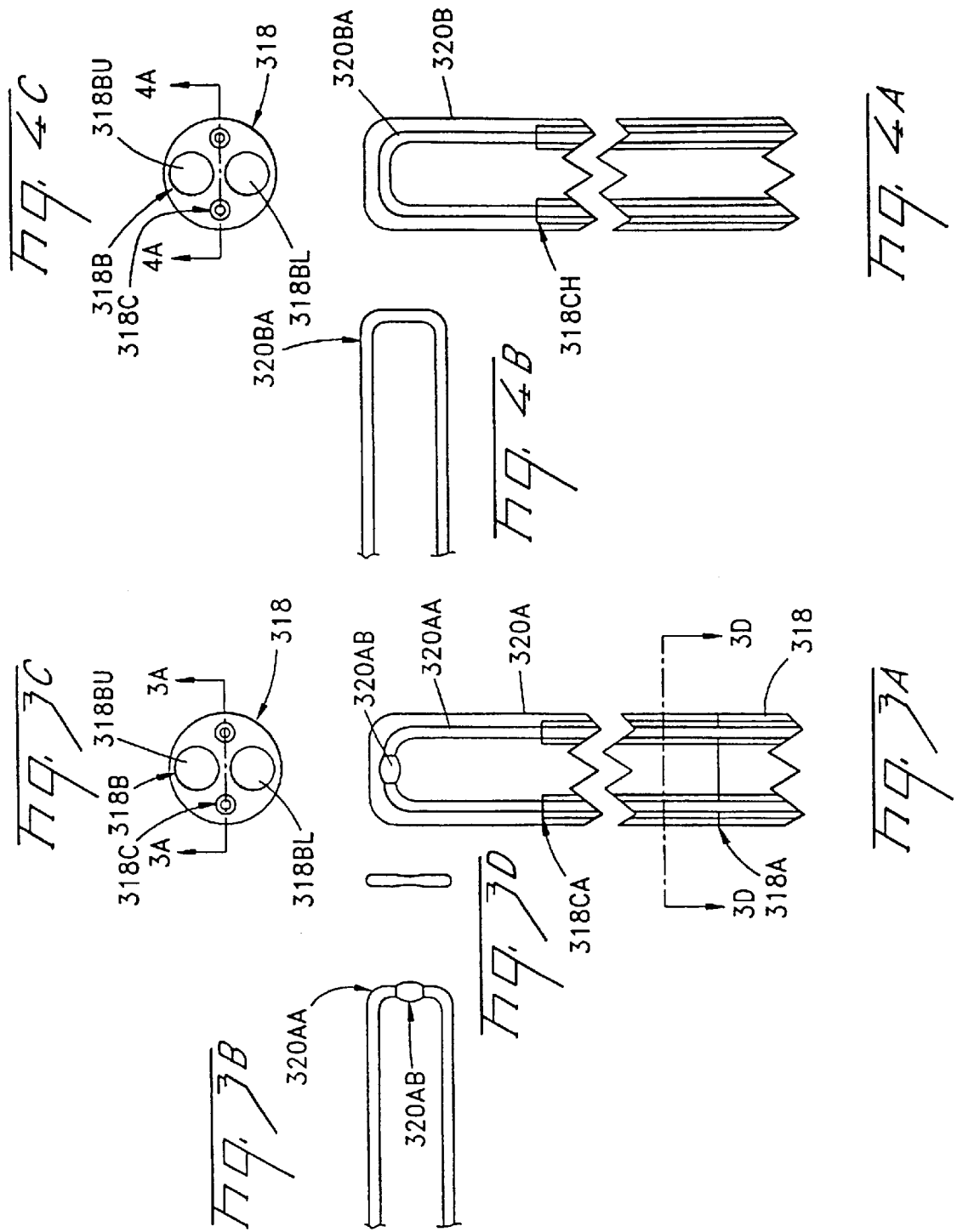

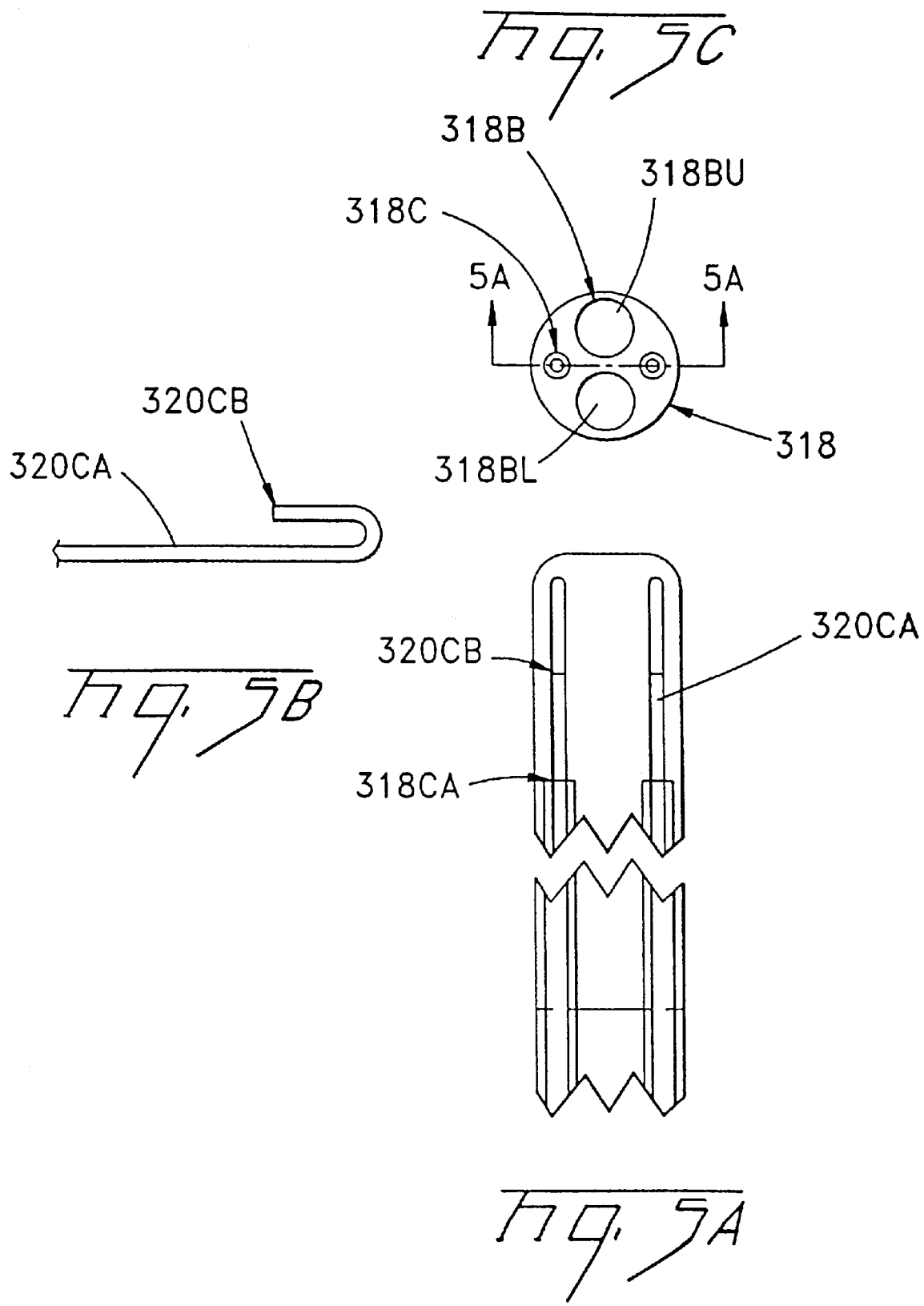

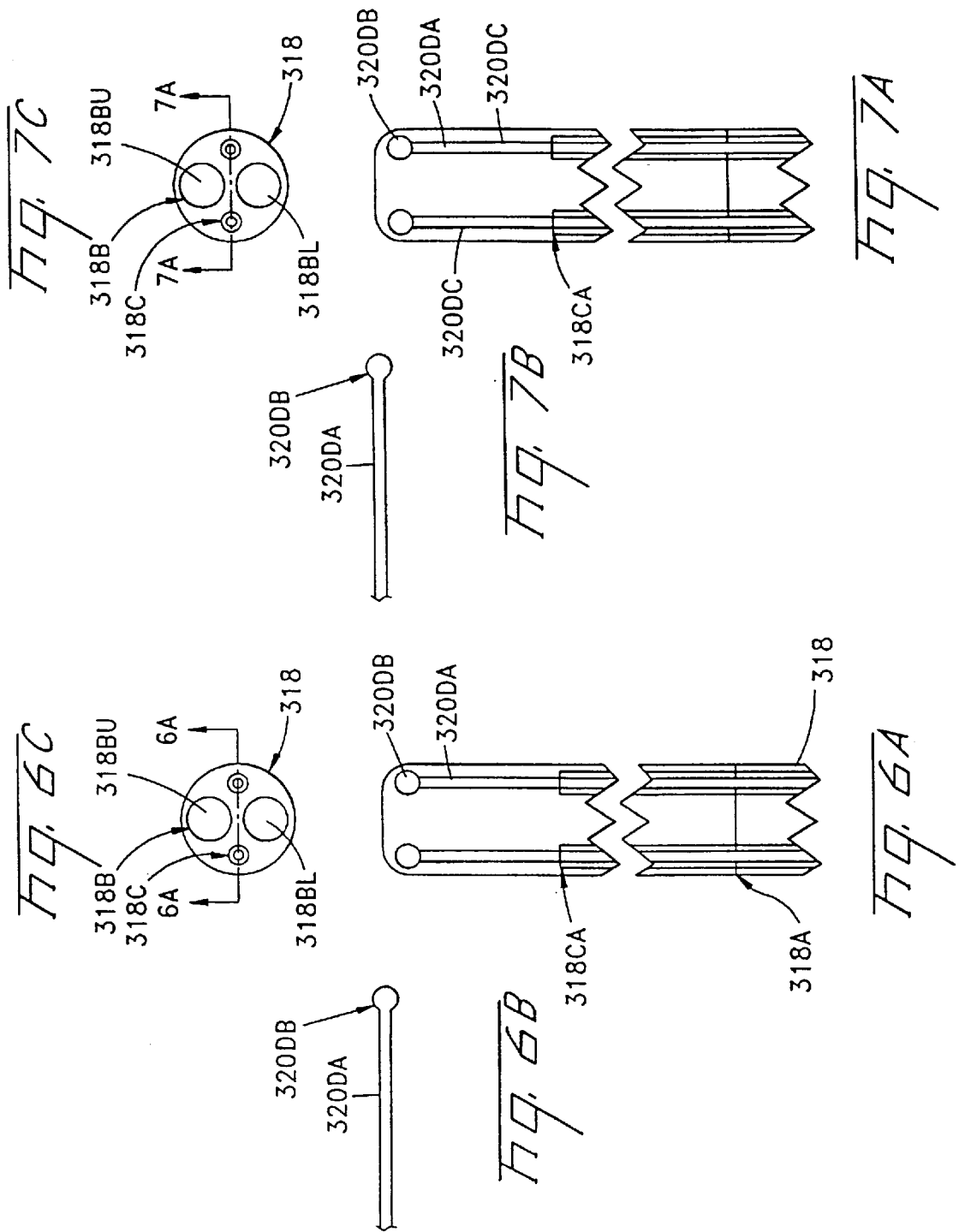

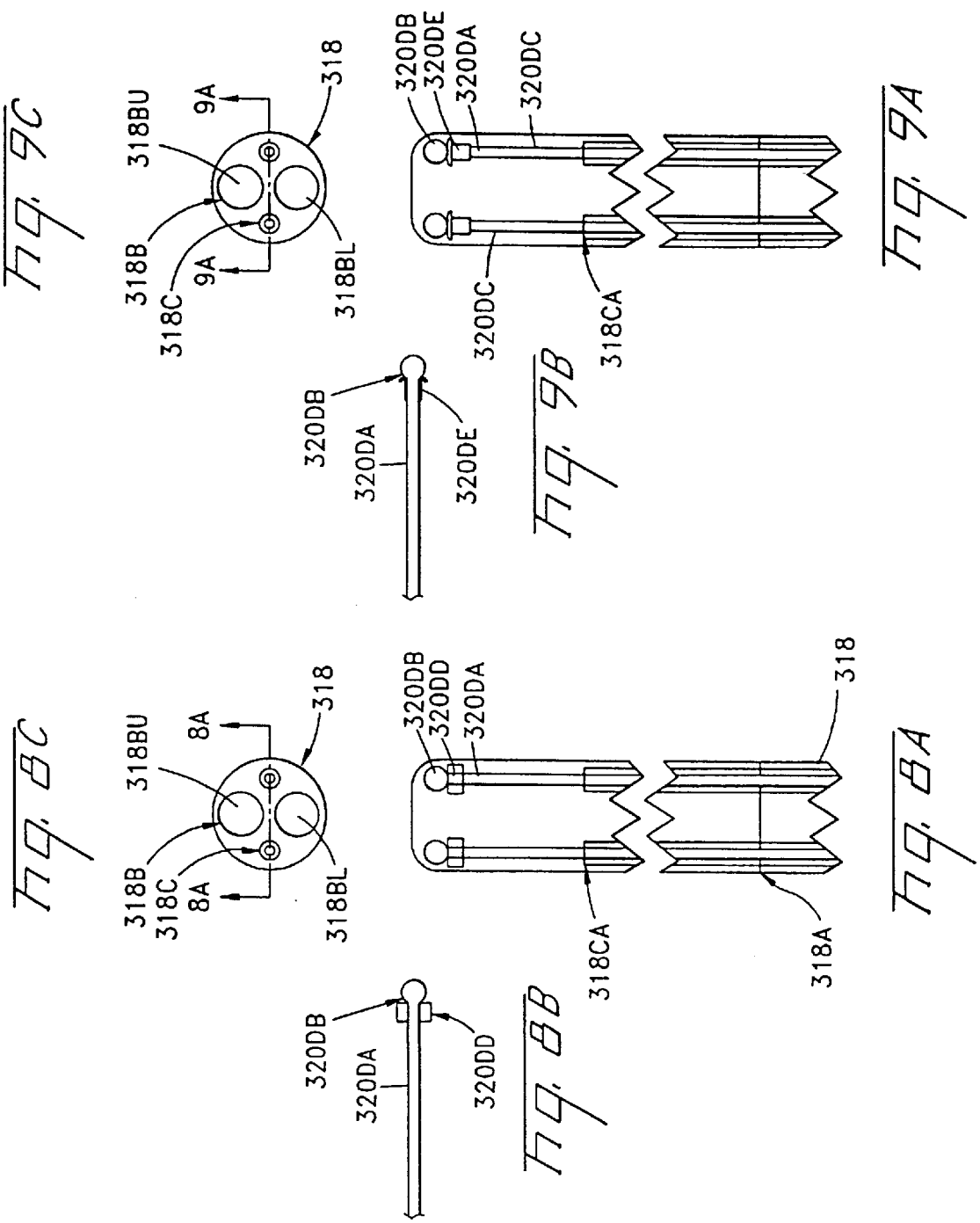

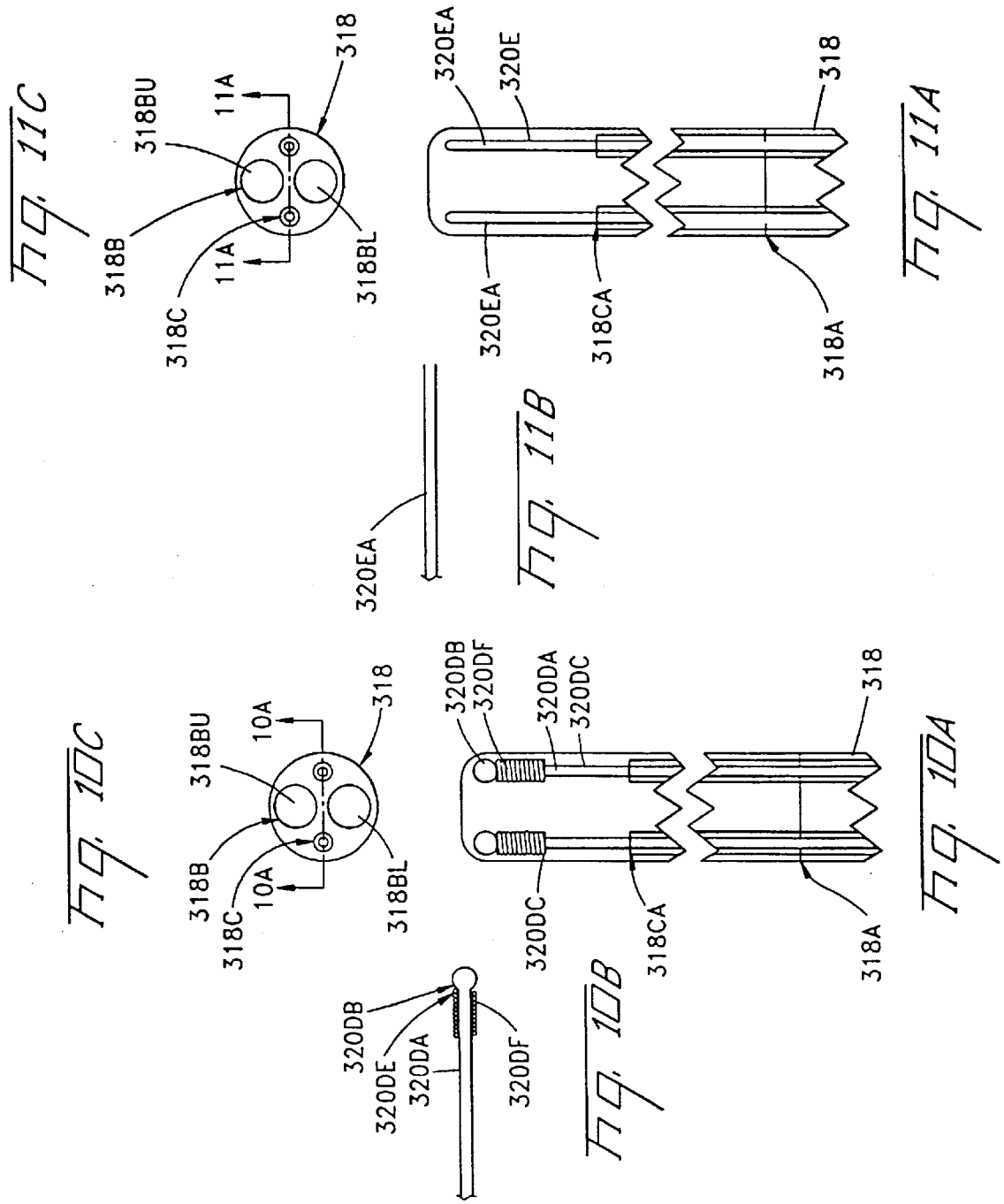

STEERABLE CATHETER

This application is a continuation-in-part, and claims the benefit under 35 U.S.C. §120, of previously filed U.S. patent application Ser. No. 08/777,548, filed Dec. 30, 1996 now U.S. Pat. No. 6,030,360.

BACKGROUND OF THE INVENTION

1. Field of the Invention

The present invention relates to a steerable catheter. More particularly, the present invention relates to a steerable catheter having an internal mechanism to enable a user to steer it left or right.

2. Description of the Prior Art

Physicians utilize catheters in many procedures to gain access to interior remote regions of the body. It is a paramount factor that the physician has total control utilizing precise movements of the catheter when inside the body. Many of the invasive procedures within the body include entry into the heart especially when an ablation therapy is utilized. Thus, total and precise control over the tip of the catheter is required. In addition, it is preferable to have the physician control both the catheter as well as any device for treatment or observing when utilized within the body.

Numerous innovations for steerable catheters have been provided in the prior art that are described as follows. Even though these innovations may be suitable for the specific individual purposes to which they address, they differ from the present invention as hereinafter contrasted.

In U.S. Pat. No. 5,456,664, titled Catheter Steering Mechanism for pulling a first catheter steering wire while simultaneously allowing a second catheter steering wire to remain static, and vice versa. The mechanism includes at least one rotatable gear and means, such as a rotatable knob, for manually rotating the gear. A first linearly slidable toothed rack is attached to the proximal end of one steering wire, and a second linearly slidable toothed rack is attached to the proximal end of the other steering wire. A toothed gear rotatable by rotation of the knob engages each of the toothed racks to move them linearly in opposite directions in response to rotation of said gear. Preferably three intermeshing gears are used so that movement of the racks are in the same direction as the rotation of the knob. Preferably the steering wires are connected to the racks by connection that transfer tension as the racks move away from the wires but allow the wires to remain static, when the rack moves toward its associated wire.

In U.S. Pat. No. 5,454,794, titled Steerable Light Diffusing Catheter, invented by Hugh L. Narcisco, Jr. and Steven C. Anderson, titled Steerable Light Diffusing Catheter, a steerable catheter is disclosed which can treat luminal surfaces such as those occurring in the vascular tree, pulmonary tree, gastrointestinal tract, urological organs, etc. with Photodynamic Therapy (PDT) or other optical diffusing treatments. The catheter, which may include an inflatable balloon portion, has a light diffusing tip which can be deflected allowing the catheter to be steered precisely. The light diffusing tip on the steerable catheter is able to gain access to and enter virtually any sub-branch of the luminal system being treated. Since this catheter does not require a guidewire lumen for insertion, the profile is reduced. A low profile device allows treatment light to be delivered to the walls of the most distal, small diameter lumen.

In U.S. Pat. No. 5,437,636, titled Steerable Catheter with Fiberoptic Scope Inserting Means, invented by Phillip J. Snoke, David S. Rowley, David G. Lincoln and Kirk W. Charles, a catheter for use in body vessels or cavities has a housing of such size as to be readily held in the hand of a user and elongate tube means having one end connected to the housing and extending outwardly therefrom and being formed of material of such a stiffness so as to maintain the elongate tube means in straight condition in the absence of an external force applied thereto, an outer end portion of the elongate tube means being flexible. Guide wires are connected to the housing by the inner ends thereof and extend outwardly therefrom through the elongate tube means. The outer ends of the guide wires are connected to the flexible outer end portion of the elongate tube means. Guide wire control means is carried by the housing and cooperates with the inner end portion of the guide wires for controlling the angular attitude of the flexible outer end portion of the elongate tube means.

In U.S. Pat. No. 5,396,880, titled Endoscope for Direct Visualization of the Spine and Epidural Space, invented by Jonathan Kagan, Roger White and David L. Brumfield, a system for direct visualization of the spine and the epidural and/or intradiscal space to facilitate diagnosis and treatment of spinal conditions and that is adapted for percutaneous introduction into the spinal space. The system includes a disposable flexible catheter, a fiberoptic bundle disposed within the catheter which is connected to a light source and camera. The bundle is removably and adjustably connected to the proximal end of the catheter to permit rotation of the bundle relative to the catheter. A mechanism for controllably deflecting the tip of the catheter is provided to vary the viewing angle of the fiber-optic bundle within and to assist in steering the catheter through the spinal space. The mechanism includes a deflection wire extending through the catheter and affixed at the distal end thereof. The proximal end of the deflection wire is affixed to a sleeve which is slidably disposed around the catheter and within a housing. The housing includes an internal flange that defines a stop surface which is contacted by the sleeve as the catheter and deflection wire is moved in a first direction. After the sleeve contacts the stop surface, further movement of the catheter in the first direction causes tension int he wire between the sleeve and the wire's securement to the catheter, thereby bending the catheter tip in the direction of the securement. The catheter can be rotated with the tip in its deflected position to provide a conical viewing region within the spinal space.

The above described patented inventions differ from the present invention because they lack one or more of the following features described and claimed in the present invention: manifold strain relief, steering dial, lumen extrusion shaft having a upper lumen extrusion shaft large lumen opening and a lower lumen extrusion shaft large lumen opening and a pair of lumen extrusion shaft small lumen openings, lumen extrusion tip, fastening means, luer lock, steering wire, catheter body lumen tubing, steering wire guide, manifold, and/or hemostatis valve/touhy borst side port.

Numerous innovations for steerable catheters have been provided in the prior art that are adapted to be used. Even though these innovations may be suitable for the specific individual purposes to which they address, they would not be suitable for the purposes of the present invention as heretofore described.

SUMMARY OF THE INVENTION

The steerable catheter was developed to satisfy a need that every pain practitioner has faced for the last 60 years. The need to directly visualize the pathology in-situ in and around the nerve roots as they make their way out of neural foramina along the axis of the spinal cord. Other means of visualizations such as Fluoroscopy, MRI, and CAT Scans cannot produce real time images of the pathology or disease and cannot clearly differentiate soft tissue pathology. Epidural endoscopy was practically impossible if performed utilizing rigid optics and the paramedian or lumbar approach. This is due to the fact that the spinal cord is encased by an articulating bone structure with minimal access possibilities. Any device with the capability to access the epidural space would have to be flexible and very small. Using miniature fiberoptic endoscopes and miniature multi lumen steerable catheters the inventor has developed a medical device that may be introduced into epidural space. The present invention allows physicians to directly visualize the epidural space of the spine and treat patients for related disease in a minimally invasive manner.

A steerable catheter is a video guided catheter having a four lumen catheter that incorporates the ability to steer the tip from left to right in one plane. The catheter consists of a body with integral steering mechanism and ports to access catheter lumens. The 0.100 inch diameter steerable catheter protrudes from the catheter body via a manifold that bifurcates the extruded catheter tubing into its four lumen components; two 0.015 inch diameter lumens for the steering wires, one 0.040 inch diameter lumen to pass the scope through the catheter, and one 0.040 inch diameter lumen for infusing fluids into the epidural space and passing instruments.

The present invention also can optionally utilize a kit consisting of disposable products that are used by the physician to access the epidural space through the sacral hiatus (tail bone). The kit contains drapes, syringe, needles, introducer set, etc.

The video system consists of a CCD camera, light source, and video monitor. The CCD camera is used to pickup the optical image from the endocoupler and convert it to an electronic signal that is sent to the video monitor. The light source consists of a bright light that is focused on the light fiber bundle to transmit light to the distal end of the scope.

The steerable catheter consists of a plastic body (handle), four lumen PeBax (plastic) extruded catheter shaft tubing, a system to bifurcate the four lumen catheter shaft to points of origin with in the housing, a mechanism to steer the catheter from left to right in one plane.

The plastic body (handle) consists of upper and lower halves that are injection molded and mate together at the central plane of the catheter body.

The catheter shaft is a four lumen extrusion with two larger 0.040 diameter holes and two smaller 0.014 diameter holes. The 0.040 diameter lumens are used to pass the Fiberscope and surgical instruments. The two 0.014 diameter lumens are used for passing the steering wires which are seated (fixed in place) at the catheter tip. The shaft is comprised of two different durometers of PeBax (plastic) tubing. The stiffer durometer is used for the 11 inch shaft and the softer durometer is used for the 1 inch tip. The function of the dual durometers for the catheter shaft is to provide a flexible top to allow for steering deflection and a stiff shaft that allows the catheter to be advanced during the procedure with out buckling.

The four lumen extruded tubing is bifurcated by a manifold located at the front of the handle assembly. From the bifurcation point the 0.040 diameter holes are ported to the rear of the catheter body via tubing which mates to standard Touhy Borst valves. At the point of bifurcation the steering wires enter the catheter shaft.

The mechanism used to steer the catheter consists of a steering dial that is trapped between the upper and lower handle in assembly and is allowed to rotate on its axis. The steering dial incorporates posts located 180 degrees apart that the steering wires are anchored to. The steering wire runs from the respective post through the point of bifurcation (at the manifold) and up the catheter shaft where it is anchored at the tip of the catheter shaft. When the steering dial is rotated it displaces the steering wires attached to the posts by means of rotational translation. This puts one wire in tension and one wire in compression. This force is transferred through the wire to the tip of the catheter causing the tip to deflect into the direction of rotation of the steering dial. Oscillating the dial from left to right causes the tip of the catheter to steer from left to right in one plane. The catheter is rotated 90 degrees to steer the catheter in a plane at right angles to the current steering plane.

There are currently other types of steerable catheters on the market. Due to the miniaturized size of the present invention, the inventor was forced to develop a new and improved steering system. Through trial and error the inventor made several different wire configurations for the steering system. The configuration of the steering wires in relation to how they are formed and anchored in the tip of the catheter is a unique feature to the present invention.

The endocoupler used in conjunction with the video guided catheter is a Fiberscope that is inserted through one of the 0.040 diameter channels in the catheter and allows the physician to view images through the end of the catheter, hence "video guided catheter". The fiberoptic endoscope relays the optical image to the endocoupler. The fiberoptic endoscope consists of an image fiber bundle and a light fiber bundle. The image fiber bundle is comprised of extremely small glass fibers (10,000 individual fibers in a ½ mm bundle) that are drawn in a coherent manner as to relay the image from the distal end of the scope to the image fiber coupler where the endoscope connects to the endocoupler. A small lens is mounted at the distal end of the scope to relay and focus the image to the fiberoptic image bundle. The light bundle is used to provide illumination at the distal end of scope for viewing. Both the image fiber bundle and the light fiber bundle are encased in flexible tubing and run parallel for the length of the scope. The two fiber bundles bifurcate at the image fiber coupler (body of the scope) where the image fiber terminates and the light fiber bundle passes to the light source. The image fiber coupler in turn is connected to the endocoupler. A collet assembly is used to make the connection between the endocoupler and the image fiber coupler of the fiberoptic endoscope.

The types of problems encountered in the prior art are steerable catheter have too large a lumen extrusion tip and lumen extrusion shaft to be utilized in small spaces. In addition, the steering mechanism of the prior art is not precise enough to navigate through complex confined matrices within the body.

In the prior art, unsuccessful attempts to solve this problem were attempted namely: steerable catheters having rotational dials. However, the problem was solved by the present invention because the steering dial works in unison with the steering wires in conjunction with the catheter body lumen tubing in conjunction with the soft lumen extrusion tip and hard lumen extrusion shaft.

Innovations within the prior art are rapidly being exploited in the field of steerable catheters.

The present invention went contrary to the teaching of the art which teaches steerable catheters having dials which do not work in unison with the steering wires in conjunction with the catheter body lumen tubing in conjunction with the soft lumen extrusion tip and hard lumen extrusion shaft.

The present invention solved a long felt need for a small steerable catheter with extremely precise ability for an user to control movement of the lumen extrusion tip.

The present invention produced unexpected results namely: the lumen extrusion tip not only has very precise control but the user can actually separate tissue as well as other objects due to inherent strength therein.

The novel features which are considered characteristic for the invention are set forth in the appended claims. The invention itself however, both as to its construction and its method of operation, together with additional objects and advantages thereof, will be best understood from the following description of the specific embodiments when read and understood in connection with the accompanying drawings.

BRIEF LIST OF REFERENCE NUMERALS UTILIZED IN THE DRAWING

310—steerable catheter (310)
312U—upper handle (312U)
312L—lower handle (312L)
314—manifold strain relief (314)
316—steering dial (316)
316L—steering dial left fastener (316L)
316R—steering dial right fastener (316R)
318—lumen extrusion shaft (318)
318A—lumen extrusion shaft connection (318A)
318B—lumen extrusion shaft large lumen opening (318B)
318BU—upper lumen extrusion shaft large lumen opening (318BU)
318BL—lower lumen extrusion shaft large lumen opening (318BL)
318C—lumen extrusion shaft small lumen opening (318C)
318CA—lumen extrusion shaft small lumen attachment (318CA)
320—lumen extrusion tip (320)
320A—looped wire lumen extrusion tip (320A)
320AA—looped wire (320AA)
320AB—looped wire radius (320AB)
320B—continuous looped wire lumen extrusion tip (320B)
320BA—continuous looped wire (320BA)
320C—formed hook wire lumen extrusion tip (320C) (Not numbered in FIG. 5A)
320CA—formed hook wire (320CA)
320CB—formed hook wire hook (320CB)
320D—ballized wire lumen extrusion tip (320D) (Not numbered in FIG. 6A)
320DA—ballized wire (320DA)
320DB—ballized wire steel ball (320DB)
320DC—ballized wire jacket (320DC)
320DD—ballized wire washer (320DD)
320DE—ballized wire eyelet (320DE)
320DF—ballized wire spring (320DF)
320E—plastic wire lumen extrusion tip (320E)
320EA—plastic wire (320EA)
322—fastening means (322) (Touhy Borst Adapter)
324—luer lock (324)
324L—left luer lock (324L)
324R—right luer lock (324R)
326L—lower handle crash pins (326L)
326U—upper handle crash pins (326U)
328—steering wire (328)
328L—left steering wire (328L)
328R—right steering wire (328R)
330—catheter body lumen tubing (330)
330L—left catheter body lumen tubing (330L)
330R—right catheter body lumen tubing (330R)
332—steering wire guide (332)
332L—left steering wire guide (332L)
332R—right steering wire guide (332L)
334—manifold (334)
336—hemostatis valve/touhy borst side port (336)

BRIEF DESCRIPTION OF THE DRAWING

FIG. 1A is a top view of a steerable catheter.

FIG. 1B is a side view of a steerable catheter.

FIG. 3A is a longitudinal cross-sectional view of a looped wire lumen extrusion tip along line 3A—3A of FIG. 3C.

FIG. 3B is a top view of a looped wire exhibiting a looped wire radius securely affixed at a front middle distal end thereof.

FIG. 3C is a cross-sectional view of a looped wire lumen extrusion tip.

FIG. 3D is a cross-sectional view of a looped wire along line 3D—3D of FIG. 3B exhibiting a looped wire radius securely affixed at a front middle distal end thereof.

FIG. 4A is a longitudinal cross-sectional view of a continuous looped wire lumen extrusion tip along line 4A—4A of FIG. 4C.

FIG. 4B is a top view of a continuous looped wire.

FIG. 4C is a cross-sectional view of a continuous looped wire lumen extrusion tip.

FIG. 5A is a longitudinal cross-sectional view of a formed hook wire lumen extrusion tip along line 5A—5A of FIG. 5C.

FIG. 5B is a top view of a formed hook wire exhibiting a formed hook wire hook at a front distal end thereof.

FIG. 5C is a cross-sectional view of a formed hook wire lumen extrusion tip.

FIG. 6A is a longitudinal cross-sectional view of a ballized wire lumen extrusion tip along line 6A—6A of FIG. 6C.

FIG. 6B is a top view of a ballized wire exhibiting a ballized wire steel ball securely affixed at a front distal end thereof.

FIG. 6C is a cross-sectional view of a ballized wire lumen extrusion tip.

FIG. 7A is a longitudinal cross-sectional view of a ballized wire lumen extrusion tip along line 7A—7A of FIG. 7C.

FIG. 7B is a top view of a ballized wire exhibiting a ballized wire steel ball securely affixed at a front distal end thereof and a ballized wire jacket securely positioned around the ballized wire.

FIG. 7C is a cross-sectional view of a ballized wire lumen extrusion tip.

FIG. 8A is a longitudinal cross-sectional view of a ballized wire lumen extrusion tip along line 8A—8A of FIG. 8C.

FIG. 8B is a top view of a ballized wire exhibiting a ballized wire steel ball securely affixed at a front distal end thereof and a ballized wire washer securely positioned around the ballized wire adjacent to the ballized wire steel ball.

FIG. 8C is a cross-sectional view of a ballized wire lumen extrusion tip.

FIG. 9A is a longitudinal cross-sectional view of a ballized wire lumen extrusion tip along line 9A—9A of FIG. 9C.

FIG. 9B is a top view of a ballized wire exhibiting a ballized wire steel ball securely affixed at a front distal end thereof and a ballized wire eyelet securely positioned around the ballized wire adjacent to the ballized wire steel ball.

FIG. 9C is a cross-sectional view of a ballized wire lumen extrusion tip.

FIG. 10A is a longitudinal cross-sectional view of a ballized wire lumen extrusion tip along line 10A—10A of FIG. 10C.

FIG. 10B is a top view of a ballized wire exhibiting a ballized wire steel ball securely affixed at a front distal end thereof and a ballized wire spring adjacent to the ballized wire steel ball.

FIG. 10C is a cross-sectional view of a ballized wire lumen extrusion tip.

FIG. 11A is a longitudinal cross-sectional view of a plastic wire lumen extrusion tip along line 11A—11A of FIG. 11C exhibiting the plastic wire securely affixed therein by a thermo-bonding process.

FIG. 11B is a top view of a plastic wire.

FIG. 11 is a cross-sectional view of a plastic wire lumen extrusion tip.

DESCRIPTION OF THE PREFERRED EMBODIMENT

Figure 2A:
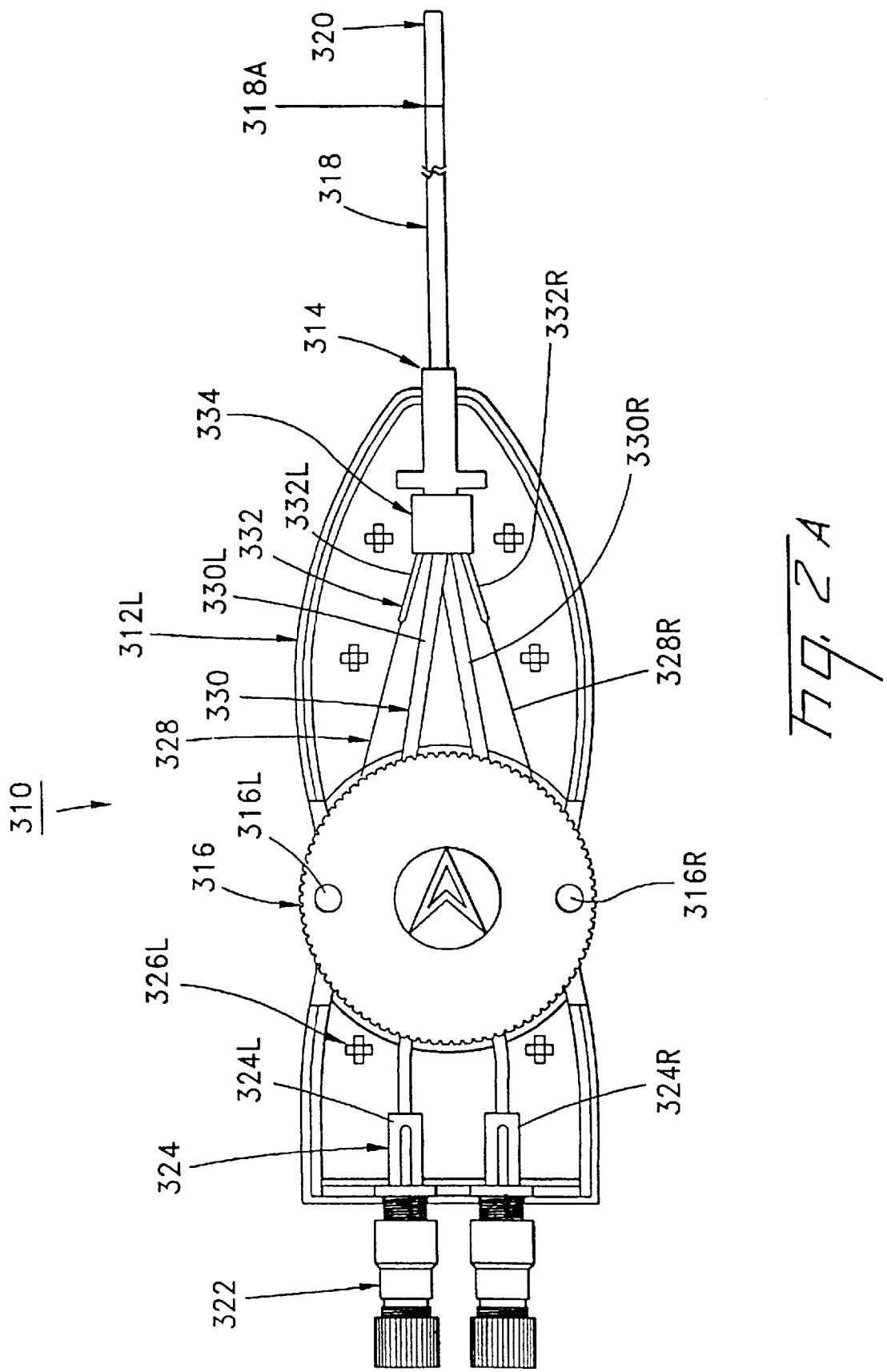
FIG. 2A is a cross-sectional top view of a steerable catheter along line 2A—2A of FIG. 1B.

Firstly, referring to FIG. 1A which is a top view of a steerable catheter (310) and FIG. 1B which is a side view of a steerable catheter (310). The steerable catheter (310) comprises a handle having a steering dial (316) rotatably mounted therein. The handle comprises an upper handle (312U) securely attached to a lower handle (312L) by upper handle crash pins (326U) and lower handle crash pins (326L), respectively. The upper handle crash pins (326U) are used to guide and align upper handle (312U) and lower handle (312L) in assembly, female portion. The lower handle crash pins (326L) are used to guide and align upper and lower handle in assembly, male portion. The lower handle (312L) is preferably ABS injection molded and designed to locate steering dial (316) and luer lock (324). The upper handle (312U) is preferably injection molded and is designed to locate steering dial (316), luer locks (324) and manifold (334). The handle is manufactured from a material selected from a group consisting of plastic, plastic composite, metal, metal alloy, fiberglass, epoxy, carbon-graphite, ceramic, wood, wood composite, rubber, and rubber composite. The handle is preferably manufactured from plastic or plastic composite material.

Figure 2B:
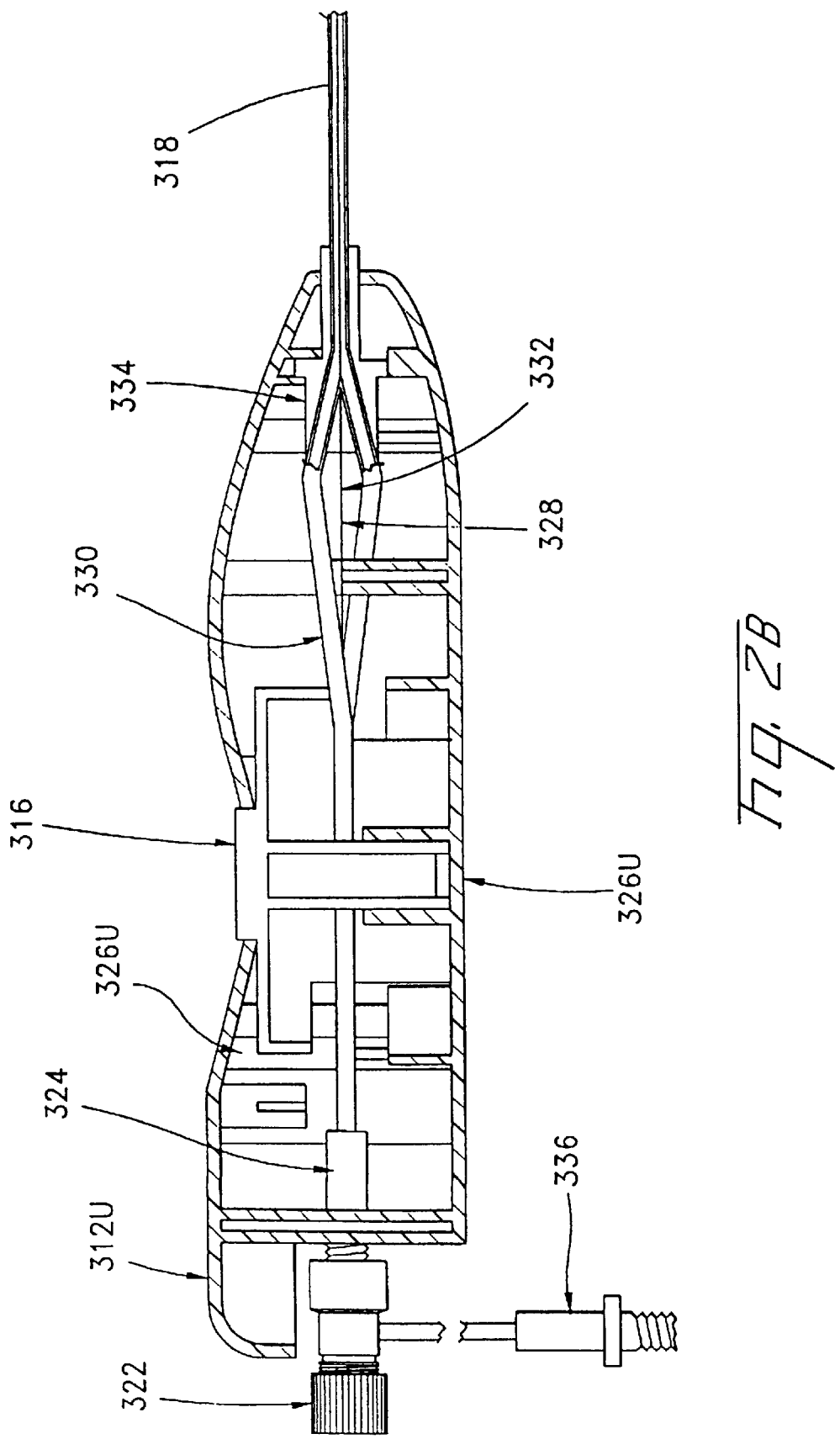
FIG. 2B is a cross-sectional side view of a steerable catheter along line 2B—2B of FIG. 1A.

Referring to FIG. 2A which is a cross-sectional top view of a steerable catheter (310) along line 2A—2A of FIG. 1B and FIG. 2B which is a cross-sectional top view of a steerable catheter (310) along line 2B—2B of FIG. 1A. The steerable catheter (310) comprises a handle. The steerable catheter (310) further comprises a manifold strain relief (314) securely mounted at a front distal end of the handle.

The steerable catheter (310) further comprises a steering dial (316) rotatably mounted within the handle. The steering dial (316) comprises a steering dial left fastener (316L) and a steering dial right fastener (316R). The steering dial (316) is used by operator to steer the lumen extrusion tip (320) back and forth in one plane. The lumen extrusion tip (320) is preferably manufactured from a softer durometer 4033 PeBax four lumen extrusion where wire (320AA, 320BA, 320CA, 320DA) is seated at lumen extrusion tip (320) by melting (tipping) plastic around the wire (320AA, 320BA, 320CA, 320DA) in the first 0.15 to 0.20 inches of tip. The steering dial (316) has molded posts with slots which are the steering dial left fastener (316L) and the steering dial right fastener (316R) that function to connect the left steering wire (328L) and the right steering wire (328R) to the steering dial (316).

The steerable tip is comprised of softer durometer 4033 PeBax and is approximately 1.25" long. At the end of the steerable tip a small piece of harder durometer 7033 PeBax, approximately 0.2" long, is fused around the steering wire to provided for a stronger bond than could be achieved with the softer durometer 4033 PeBax.

The steerable catheter (310) further comprises a lumen extrusion shaft (318) securely fastened at a rear distal end to the manifold strain relief (314). The lumen extrusion shaft (318) comprises at least one lumen extrusion shaft large lumen opening (318B) and at least one lumen extrusion shaft small lumen opening (318C) contained therein.

The steerable catheter (310) further comprises a lumen extrusion tip (320) securely fastened at a front distal end of the lumen extrusion shaft (318) by a lumen extrusion shaft connection (318A). The lumen extrusion shaft connection (318A) is a fusion joint where softer durometer tip is fused to harder durometer shaft. The lumen extrusion tip (320) is selected from a group consisting of looped wire lumen extrusion tip (320A), continuous looped wire lumen extrusion tip (320B), formed hook wire lumen extrusion tip (320C), ballized wire lumen extrusion tip (320D), and plastic wire lumen extrusion tip (320E).

The steerable catheter (310) further comprises a manifold (334) securely fastened at a rear end of the manifold strain relief (314). The manifold (334) is a bifurcation point where transition is made between integral four lumen extrusion to individual tubes. The manifold strain relief (314) portion of manifold (334) extends beyond handle (312U, 312L) assembly.

The steerable catheter (310) further comprises at least one luer lock (324) securely mounted at a rear distal end of the handle. The luer lock (324) is a transition coupling between catheter body lumen tubing (330) and hemostatis valve/touhy borst with side port (336). Wings and flanges on luer lock (324) sit in slots that are molded into the upper handle (312U) and the lower handle (312L) to capture the luer lock and hold the hemostatis valve/touhy borst side port (336) in place.

The luer lock (324) comprises a fastening means (322) removably attached to a rear end thereof. The fastening means (322) is further connected to a hemostatis valve/touhy borst with side port (336). The hemostatis valve/touhy borst with side port (336) is used to pass and seal around scopes and instruments inserted through the steerable catheter. The side port is used to infuse saline to distend the epidural space and pass other fluids through the steerable catheter lumen. The hemostatis valve/touhy borst with side port (336) are used to pass and seal around scopes and instruments inserted through the steerable catheter (310).

The steerable catheter (310) further comprises a steering wire (328) securely fastened at a rear distal end to the steering dial (316). The steering wire (328) is slidably mounted within the manifold (334) and the manifold strain relief (314) and the lumen extrusion shaft (318). The lumen extrusion shaft (318) is preferably manufactured from a harder durometer 7033 PeBax four lumen extrusion tubing. The steering wire (328) comprises a left steering wire (328L) securely fastened at a rear distal end to the steering dial left fastener (316L) and a right steering wire (328R) securely fastened at a rear distal end to the steering dial right fastener (316R). The steering wire (328) is slidably positioned within the at least one lumen extrusion shaft small lumen opening (318C). The steering wire (328) is securely affixed at a front end to the lumen extrusion shaft (318) by a lumen extrusion shaft small lumen attachment (318CA). The steering wire (328) terminates at a front distal end wire lumen extrusion tip which is securely mounted within the lumen extrusion tip (320). The steering wire guide (332) is preferably composed of a left steering wire guide (332L) and a right steering wire guide (332L). The left steering wire guide (332L) and the right steering wire guide (332L) are tubing used to pass the left steering wire (328L) and the right steering wire (328R), respectively, from lumen extrusion shaft (318) into catheter body via the manifold (334). The left steering wire (328L) is slidably positioned within a left steering wire guide (332L) which is securely attached to a rear end of the manifold (334) and the right steering wire (328R) is slidably positioned within right steering wire guide (332L) which is securely attached to a rear end of the manifold (334). The steering wire (328) is seated in lumen extrusion tip (320) and passes through extruded lumen extrusion shaft small lumen opening (318C) which are wire channels where they exit from the manifold (334) and run to the steering dial (316).

The steerable catheter (310) further comprises a catheter body lumen tubing (330) securely fastened at a rear distal end to the least one luer lock (324) and securely fastened at a front distal end to the at least one lumen extrusion shaft large lumen opening (318B). A front end of the catheter body lumen tubing (330) is securely mounted within the manifold (334). The catheter body lumen tubing (330) comprises a left catheter body lumen tubing (330L) securely attached at a rear distal end to a left luer lock (324L) and attached at a front distal end to an upper lumen extrusion shaft large lumen opening (318BU) within the manifold (334). The catheter body lumen tubing (330) further comprises a right catheter body lumen tubing (330R) securely attached at a rear distal end to a right luer lock (324R) and attached at a front distal end to a lower lumen extrusion shaft large lumen opening (318BL) within the manifold (334). The catheter body lumen tubing (330) connects the four lumen extrusion scope and working channel lumens which are lumen extrusion shaft large lumen openings (318B) and lumen extrusion shaft small lumen openings (318C) to the respective luer lock (324) via bifurcation point in the manifold (334).

Referring to FIG. 3A which is a longitudinal cross-sectional view of a looped wire lumen extrusion tip (320A) along line 3A—3A of FIG. 3C and FIG. 3C which is a cross-sectional view of a looped wire lumen extrusion tip (320A). The cross-sectional view of a looped wire lumen extrusion tip (320A) is the preferred embodiment as used in the steerable catheter (310). This approach uses a continuous stainless steel steering wire that runs up one lumen extrusion shaft small lumen opening (318C) of the lumen extrusion tip (320), is bent 180 degrees, and runs back down the other lumen extrusion shaft small lumen opening (318C) of the lumen extrusion shaft (318). The distal end of the lumen extrusion tip (320) is heated to melt the plastic surrounding the looped wire (320AA) which seats the looped wire (320AA) therein.

Referring to FIG. 3B which is a top view of a looped wire (320AA) exhibiting a looped wire radius (320AB), or coined portion securely affixed at a front middle distal end thereof. FIG. 3D which is a cross-sectional view of a looped wire (320AA) along line 3D—3D of FIG. 3B exhibiting a looped wire radius (320AB) securely affixed at a front middle distal end thereof. The design employs a looped wire (320AA) with a looped wire radius (320AB) that is formed in the center of the lumen extrusion tip (320). This allows a 0.010" diameter looped wire (320AA) to pass between the 0.005" wall thickness of the two lumen extrusion shaft large lumen openings (318B). The looped wire radius (320AB) is formed by coining the center of the looped wire (320AA) bend between to 0.040" diameter rods on a forming tool.

Referring to FIG. 4A which is a longitudinal cross-sectional view of a continuous looped wire lumen extrusion tip (320B) along line 4A—4A of FIG. 4C, FIG. 4B which is a top view of a continuous looped wire (320BA), and FIG. 4C which is a cross-sectional view of a continuous looped wire lumen extrusion tip (320B). The continuous looped wire lumen extrusion tip (320B) uses a continuous stainless steel steering continuous looped wire (320BA) that runs up one lumen extrusion shaft small lumen opening (318C) of the lumen extrusion tip (320), is bent 180 degrees, and runs back down the other lumen extrusion shaft small lumen opening (318C) of the catheter body lumen tubing (330). The design employs 0.005" diameter wire to pass between the 0.005" wall thickness of the two lumen extrusion shaft large lumen openings (318B). The distal end of the lumen extrusion tip (320) is heated to melt the plastic surrounding the continuous looped wire (320BA) which seats the continuous looped wire (320BA) therein.

Referring to FIG. 5A which is a longitudinal cross-sectional view of a formed hook wire lumen extrusion tip (320C) along line 5A—5A of FIG. 5C, FIG. 5B which is a top view of a formed hook wire (320CA) exhibiting a formed hook wire hook (320CB) at a front distal end thereof, and FIG. 5C which is a cross-sectional view of a formed hook wire lumen extrusion tip (320C). The formed hook wire lumen extrusion tip (320C) uses two separate stainless steel steering formed hook wire (320CA) that run up the lumen extrusion shaft small lumen opening (318C) of the four lumen extrusion catheter body lumen tubing (330). The design employs two 0.010" diameter formed hook wires (320CA) with small formed bends on the end to create a "formed wire hook (320CB)". The distal end of the lumen extrusion tip (320) is heated to melt the plastic surrounding the continuous formed hook wires (320CA) and respective formed hook wire hooks (320CB) which seats them therein.

Referring to FIG. 6A which is a longitudinal cross-sectional view of a ballized wire lumen extrusion tip (320D) along line 6A—6A of FIG. 6C, FIG. 6B which is a top view of a ballized wire (320DA) exhibiting a ballized wire steel ball (320DB) securely affixed at a front distal end thereof, and FIG. 6C which is a cross-sectional view of a ballized wire lumen extrusion tip (320D). The ballized wire lumen extrusion tip (320D) uses two separate stainless steel ballized wires (320DA) that run up the lumen extrusion shaft small lumen openings (318C) of the four lumen extrusion catheter body lumen tubing (330). The design employs two 0.010" diameter ballized wires (320DA) with 0.020" diameter ballized wire steel balls (320DB) welded to the distal end of the ballized wires (320DA). The distal end of the lumen extrusion tip (320) is heated to melt the plastic surrounding the ballized wires (320DA) and respective ballized wire steel ball (320DB) which seats them therein.

Referring to FIG. 7A which is a longitudinal cross-sectional view of a ballized wire lumen extrusion tip (320D)

along line 7A—7A of FIG. 7C, FIG. 7B which is a top view of a ballized wire (320DA) exhibiting a ballized wire steel ball (320DB) securely affixed at a front distal end thereof and a ballized wire jacket (320DC) securely positioned around the ballized wire (320DA), and FIG. 7C which is a cross-sectional view of a ballized wire lumen extrusion tip (320D). This embodiment of the ballized wire lumen extrusion tip (320D) uses two separate stainless steel ballized wires (320DA) that run up the lumen extrusion shaft small lumen openings (318C) of the four lumen extrusion catheter body lumen tubing (330). The design employs two 0.010" diameter ballized wires (320DA) with 0.020" diameter ballized wire steel balls (320DB) welded to the distal end of the ballized wires (320DA). UV curable epoxy glue is injected into the lumen extrusion shaft small lumen openings (318C) prior to pulling the ballized wire steel balls (320DB) into the extrusion. The epoxy ballized wire jacket (320DC) is UV cured and the distal end of lumen extrusion tip (320) is heated to melt the plastic surrounding the ballized wires (320DA), respective ballized wire steel ball (320DB) and respective ballized wire jacket (320DC) which seats them therein.

Referring to FIG. 8A which is a longitudinal cross-sectional view of a ballized wire lumen extrusion tip (320D) along line 8A—8A of FIG. 8C, FIG. 8B which is a top view of a ballized wire (320DA) exhibiting a ballized wire steel ball (320DB) securely affixed at a front distal end thereof and a ballized wire washer (320DD) securely positioned around the ballized wire (320DA) adjacent to the ballized wire steel ball (320DB), and FIG. 8C which is a cross-sectional view of a ballized wire lumen extrusion tip (320D). The ballized wire lumen extrusion tip (320D) uses two separate stainless steel ballized wires (320DA) that run up the lumen extrusion shaft small lumen openings (318C) of the four lumen extrusion catheter body lumen tubing (330). The design employs two 0.010" diameter ballized wires (320DA) with 0.020" diameter ballized wire steel balls (320DB) welded to the distal end of the ballized wires (320DA). A ballized wire washer (320DD) with a 0.024" outside diameter and a 0.012" inside diameter is slid over each of the ballized wires (320DA) and up to the ballized wire steel ball (320DB) and pulled into the lumen extrusion shaft small lumen openings (318C) of the lumen extrusion tip (320). The distal end of the lumen extrusion tip (320) is heated to melt the plastic surrounding the ballized wires (320DA), respective ballized wire steel ball (320DB), and respective ballized wire washer (320DD) which seats them therein Referring to FIG. 9A which is a longitudinal cross-sectional view of a ballized wire lumen extrusion tip (320D) along line 9A—9A of FIG. 9C, FIG. 9B which is a top view of a ballized wire (320DA) exhibiting a ballized wire steel ball (320DB) securely affixed at a front distal end thereof and a ballized wire eyelet (320DE) securely positioned around the ballized wire (320DA) adjacent to the ballized wire steel ball (320DB), and FIG. 9C which is a cross-sectional view of a ballized wire lumen extrusion tip (320D). The ballized wire lumen extrusion tip (320D) uses two separate stainless steel ballized wires (320DA) that run up the lumen extrusion shaft small lumen openings (318C) of the four lumen extrusion catheter body lumen tubing (330). The design employs two 0.010" diameter ballized wires (320DA) with 0.020" diameter ballized wire steel balls (320DB) welded to the distal end of the ballized wires (320DA). A stainless steel ballized wire eyelet (320DE) with a 0.024" outside diameter and a 0.012" inside diameter is slid over each of the ballized wires (320DA) and up to each of the ballized wire steel balls (320DB) and pulled into the lumen extrusion shaft small lumen openings (318C) of the lumen extrusion tip (320). The distal end of the lumen extrusion tip (320) is heated to melt the plastic surrounding the ballized wires (320DA), respective ballized wire steel ball (320DB), and respective ballized wire eyelet (320DE) which seats them therein Referring to FIG. 10A which is a longitudinal cross-sectional view of a ballized wire lumen extrusion tip (320D) along line 10A—10A of FIG. 10C, FIG. 10B which is a top view of a ballized wire (320DA) exhibiting a ballized wire steel ball (320DB) securely affixed at a front distal end thereof and a ballized wire eyelet (320DE) securely positioned around the ballized wire spring (320DF) adjacent to the ballized wire steel ball (320DB), and FIG. 10C which is a cross-sectional view of a ballized wire lumen extrusion tip (320D). The ballized wire lumen extrusion tip (320D) uses two separate stainless steel ballized wires (320DA) that run up the lumen extrusion shaft small lumen openings (318C) of the four lumen extrusion catheter body lumen tubing (330). The design employs two 0.010" diameter ballized wires (320DA) with 0.020" diameter ballized wire steel balls (320DB) welded to the distal end of the ballized wires (320DA). A stainless steel ballized wire spring (320DF) with a 0.024" outside diameter and a 0.012" inside diameter is slid over each of the ballized wires (320DA) and up to each of the ballized wire steel balls (320DB) and pulled into the lumen extrusion shaft small lumen openings (318C) of the lumen extrusion tip (320). The distal end of the lumen extrusion tip (320) is heated to melt the plastic surrounding the ballized wires (320DA), respective ballized wire steel ball (320DB), and respective ballized wire spring (320DF) which seats them therein Referring to FIG. 11A which is a longitudinal cross-sectional view of a plastic wire lumen extrusion tip (320E) along line 10A—10A of FIG. 11C exhibiting the plastic wire (320EA) securely affixed therein by a thermo-bonding process, FIG. 11B which is a top view of a plastic wire (320EA), and FIG. 11C which is a cross-sectional view of a plastic wire lumen extrusion tip (320E). This embodiment uses two separate steering plastic wires (320EA) that run up the lumen extrusion shaft small lumen openings (318C) of the four lumen extrusion catheter body lumen tubing (330). The design employs two 0.010" diameter plastic wires (320EA) that are pulled into the lumen extrusion shaft small lumen openings (318C) of the lumen extrusion tip (320). The distal end of the plastic wire lumen extrusion tip (320E) is heated to melt the plastic wires (320EA) into the surrounding plastic wire lumen extrusion tip (320E) which seats the plastic wires (320EA) therein.

It will be understood that each of the elements described above, or two or more together, may also find a useful application in other types of constructions differing from the type described above.

While the invention has been illustrated and described as embodied in a steerable catheter, it is not intended to be limited to the details shown, since it will be understood that various omissions, modifications, substitutions and changes in the forms and details of the device illustrated and in its operation can be made by those skilled in the art without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed as new and desired to be protected by Letters Patent is set forth in the appended claims:

1. A steerable catheter comprising:
   (a) a handle having a first end comprising first and second ports for allowing passage of instruments therethrough, and a second end generally opposite said first end;
   (b) a steering dial rotatably mounted within said handle;
   (c) a catheter shaft extending from the second end of said handle, said catheter shaft comprising:
      (i) a first shaft segment having a first stiffness, said first shaft segment having a rear distal end coupled to said handle, and a front distal end opposite said rear distal end;
      (ii) a tip segment having a second stiffness less than said first stiffness, said tip segment having a first end fused to the front distal end of said first shaft segment, and a second end opposite said first end;
      (iii) an end segment fused to the second end of said tip segment, said end segment having a greater stiffness than said tip segment;
      (iv) a first steering wire lumen extending lengthwise through said first shaft segment, said tip segment, and at least a portion of said end segment;
      (v) a second steering wire lumen extending lengthwise through said first shaft segment, said tip segment, and at least a portion of said end segment, said second steering wire lumen extending generally parallel to and diametrically separated from said first steering wire lumen; and
      (vi) first and second instrument passage lumens extending lengthwise through said first shaft segment, said tip segment, and said end segment;
   (d) a steering wire having a first end coupled to a first point of said steering dial, a looped portion extending through said first steering wire lumen and said second steering wire lumen, and a second end coupled to a second point of said steering dial, wherein said looped portion comprises a coined portion adjacent said end segment and extending between said first and second instrument passage lumens, whereby rotation of said steering dial causes said tip segment of said catheter shaft to flex;
   (e) a manifold having first and second passages therethrough, said first passage communicating with said first instrument passage lumen, and said second passage communicating with said second instrument passage lumen; and
   (f) first and second tubing segments, said first tubing segment connecting said first port to said first passage of said manifold, and said second tubing segment connecting said second port to said second passage of said manifold.

2. The steerable catheter of claim 1, wherein said first and second ports comprise valves for sealing around instruments inserted therethrough.

3. The steerable catheter of claim 1, wherein said first and second ports comprise flush ports for infusing fluid through said first and second instrument passage lumens.

4. A steerable catheter comprising:
   (a) a handle comprising a steering actuator;
   (b) a catheter shaft having a rear distal end coupled to said handle and a free end opposite said rear distal end, said catheter shaft further defining first and second steering wire lumens extending lengthwise therethrough; and
   (c) a loop of steering wire having a first end coupled to a first point of said steering actuator, a central portion extending through said first and second steering wire lumens, and a second end coupled to a second point of a steering actuator, wherein said central portion of said loop of steering wire comprises a coined portion adjacent said free end of said catheter shaft.

5. The catheter of claim 4, wherein said catheter shaft further defines first and second instrument passage lumens, and wherein said coined portion of said steering wire extends between said first and second instrument passage lumens.

* * * * *